(12) United States Patent
Holland et al.

(10) Patent No.: US 9,173,825 B2
(45) Date of Patent: Nov. 3, 2015

(54) PERSONAL CARE COMPOSITIONS COMPRISING SULFATED POLOXAMERS AND METHODS OF MAKING AND USING SAME

(71) Applicant: BASF SE, Ludwigshafen (DE)

(72) Inventors: Richard Holland, Flanders, NJ (US); Eduardo Caballero, Bethlehem, PA (US); James S. Dailey, Grosse Ile, MI (US); David Durocher, Westland, MI (US); Ashish Taneja, Ann Arbor, MI (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/948,376

(22) Filed: Jul. 23, 2013

(65) Prior Publication Data

US 2014/0030195 A1 Jan. 30, 2014

Related U.S. Application Data

(60) Provisional application No. 61/676,428, filed on Jul. 27, 2012.

(51) Int. Cl.
| | |
|---|---|
| *A61K 8/46* | (2006.01) |
| *A61Q 19/00* | (2006.01) |
| *A61K 8/60* | (2006.01) |
| *A61Q 11/00* | (2006.01) |
| *A61K 8/86* | (2006.01) |

(52) U.S. Cl.
CPC .................. *A61K 8/463* (2013.01); *A61K 8/604* (2013.01); *A61K 8/86* (2013.01); *A61Q 11/00* (2013.01); *A61Q 19/00* (2013.01); *A61K 2800/596* (2013.01)

(58) Field of Classification Search
USPC ...................................... 516/14; 510/125, 127
See application file for complete search history.

(56) References Cited

U.S. PATENT DOCUMENTS

| | | | |
|---|---|---|---|
| 4,077,917 A * | 3/1978 | Panzer ............................ | 516/14 |
| 4,304,691 A | 12/1981 | Farmer et al. | |
| 5,296,215 A | 3/1994 | Burke et al. | |
| 5,883,058 A * | 3/1999 | Wells et al. .................... | 510/127 |
| 2007/0107747 A1 | 5/2007 | Hill et al. | |
| 2007/0224155 A1 | 9/2007 | Brumbaugh et al. | |
| 2008/0113895 A1 | 5/2008 | Tamareselvy et al. | |
| 2011/0243860 A1 | 10/2011 | Narasimhan et al. | |

OTHER PUBLICATIONS

PCT International Preliminary Report on Patentability dated Jan. 27, 2015.

* cited by examiner

*Primary Examiner* — Walter Webb
(74) *Attorney, Agent, or Firm* — Sheila A. Loggins

(57) ABSTRACT

Provided are personal care compositions comprising a first surfactant comprising sodium lauryl sulfate and a second surfactant having a structure represented by

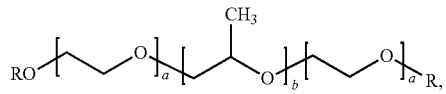

wherein each a has a value of about 1 to about 110, b has a value of about 16 to about 70, and at least one R group is $SO_3$, and the other R group is $SO_3$ or hydrogen. Also provided are methods of producing personal care compositions and methods of ameliorating skin or mucosal membrane irritation due to sodium lauryl sulfate.

18 Claims, 8 Drawing Sheets

PERSONAL CARE COMPOSITIONS COMPRISING SULFATED POLOXAMERS AND METHODS OF MAKING AND USING SAME

TECHNICAL FIELD

Aspects of the invention generally relate to personal care compositions, and specifically to compositions containing sulfated surfactants.

BACKGROUND

Sodium lauryl sulfate (SLS) is a very commonly used foaming agent in oral care products, in particular, toothpaste. SLS offers certain properties over other surfactants that make it desirable for the use in oral applications. These properties include high foaming properties, low oral toxicity, and low cost. However, SLS has several disadvantages that can greatly limit its use in oral care applications. These disadvantages include foam suppression by divalent cations such as $Ca^{2+}$, and the tendency to denature proteins. Protein denaturation is a particular problem that can lead to skin irritation and incompatibility with proteinacious materials. This means that SLS may not be favorably combined with proteinacious additives, which may be desirable, including enzymes and beneficial bacteria.

There have been several attempts to address these problems, including use of alkyl polyglucosides. Alkyl polyglucosides (APGs) are high foaming surfactants employed in a number of personal care applications, including oral care. APGs are very mild to proteinacious surfaces and are known to improve the foaming properties of SLS in the presence of hard water cations. However, APGs have a bitter aftertaste which can limit their use in oral care application.

Therefore, there exists a need to develop surface active materials that can mitigate the effect of SLS on protein without negatively impacting foam. In particular, for oral care applications, there also exists a need for surfactants which solve the above problems but also do not negatively impact taste.

SUMMARY

One aspect of the invention relates to a personal care composition. The personal care composition comprises: a first surfactant comprising sodium lauryl sulfate; and a second surfactant having a structure represented by

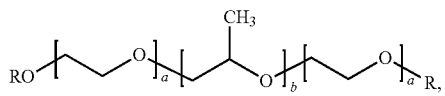

wherein each a has a value of about 1 to about 110, b has a value of about 16 to about 70, and at least one R group is $SO_3$, and the other R group is $SO_3$ or hydrogen. Various embodiments are listed below. It will be understood that the embodiments listed below may be combined not only as listed below, but in other suitable combinations in accordance with the scope of the invention.

For example, there are many variations related to the second surfactant. In one or more embodiments, both R groups are $SO_3$. In some embodiments, the second surfactant has a ratio of a to b of about 10:90 to about 30:70. In alternative embodiments, the second surfactant has a ratio of a to b of about 60:40 to about 80:20.

There are also variations in composition, including in the relative amounts of components. Thus, for example, in one or more embodiments, the first and second surfactants are present in a ratio of about 1:2 to about 4:1, or about 1:1 to about 3:1. In some embodiments relates to a personal care composition further comprising alkyl polyglucoside. In some embodiments the first surfactant, second surfactant and alkyl polyglucoside are present in a ratio of about 1:1:1 to about 3:1:1. Some embodiments relate to wherein the personal care composition further comprises a biomolecule.

In one or more embodiments, the personal care composition is an oral care composition. Thus, in one or more embodiments, the personal care composition further comprises an abrasive and/or fluoride.

Another aspect of the invention relates to a method of ameliorating skin or mucosal membrane irritation due to sodium lauryl sulfate. The method comprises: providing a composition that contacts skin or mucosal membrane upon use, the composition comprising a first surfactant comprising sodium lauryl sulfate and a second surfactant having a structure represented by

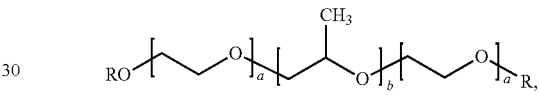

wherein each a has a value of about 1 to about 110, b has a value of about 16 to about 70, and at least one R group is $SO_3$, and the other R group is $SO_3$ or hydrogen; and wherein the second surfactant is present in an amount that is effective to ameliorate irritation of the skin or mucosal membrane. In one or more embodiments, upon contact with the skin or mucosal membrane, the composition results in less skin or mucosal membrane irritation as compared to contact by the skin or mucosal membrane with a comparable composition comprising sodium lauryl sulfate without the second surfactant.

Furthermore, any of the variants in the composition may also apply here. Thus, for example, in some embodiment, both R groups are $SO_3$. In one or more embodiments, the first and second surfactants are present in a ratio of about 1:2 to about 4:1.

A third aspect of the invention relates to a method of making a personal care composition. The method comprises adding to a pharmaceutically or cosmetically acceptable base, a first surfactant comprising sodium lauryl sulfate and a second surfactant having a structure represented by

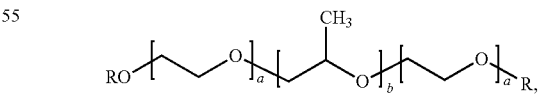

wherein each a has a value of about 1 to about 110, b has a value of about 16 to about 70, and at least one R group is $SO_3$, and the other R group is $SO_3$ or hydrogen.

In one or more embodiments, the method further comprises adding alkyl polyglucoside to the base. In some embodiments, the method further comprises adding a biomolecule to the base. One or more embodiments relate to where the first and second surfactants are present in a ratio of about 1:2 to about 4:1. In some embodiments, the personal care composition is an oral care composition.

BRIEF DESCRIPTION OF THE DRAWINGS

So that the manner in which the above recited features of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
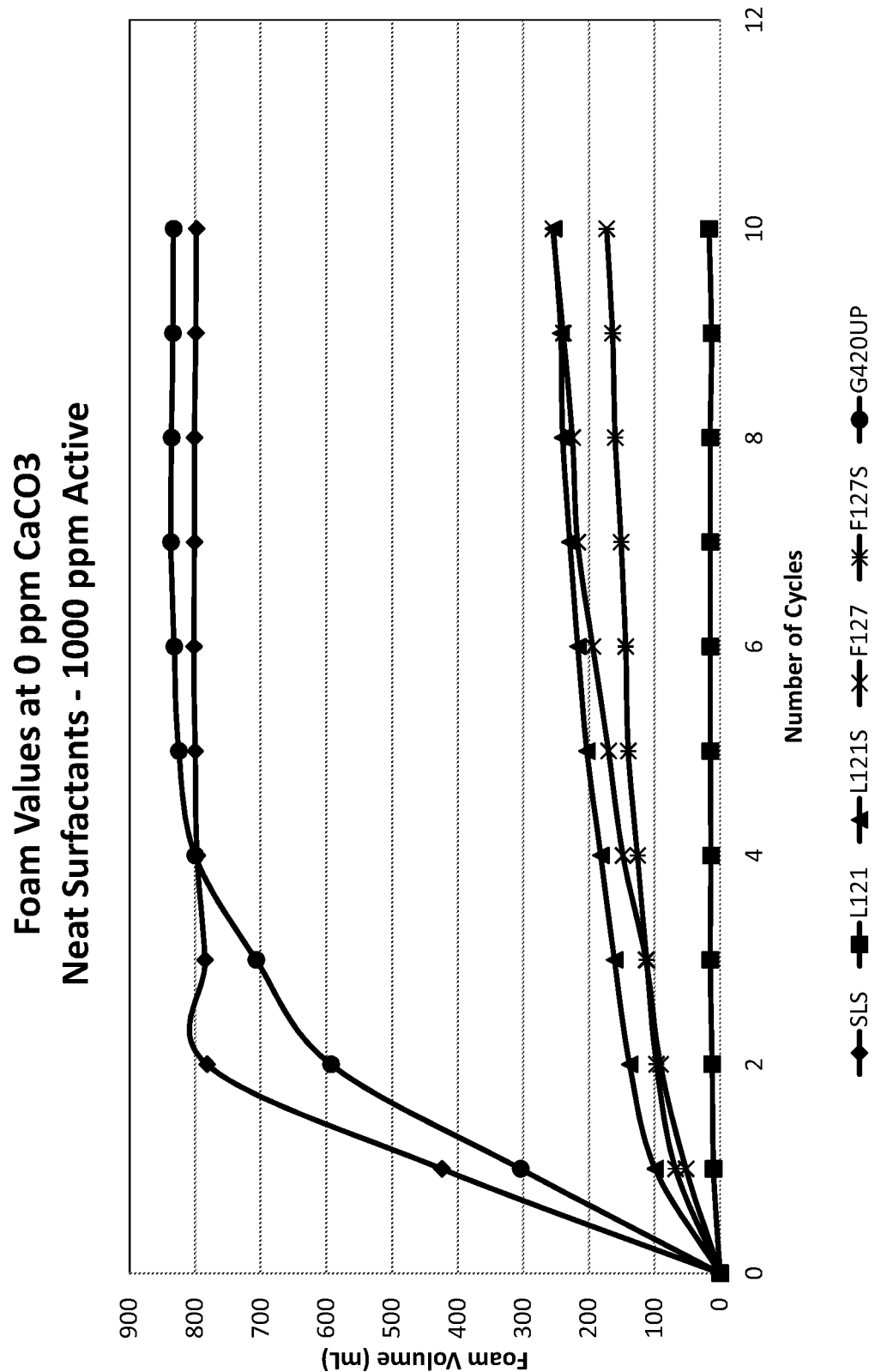
FIG. 1 shows the foam values in soft water of sodium lauryl sulfate, an AGP, several unsulfated poloxamers and sulfated poloxamers according to one or more embodiments of the invention.

Before describing several exemplary embodiments of the invention, it is to be understood that the invention is not limited to the details of construction or process steps set forth in the following description. The invention is capable of other embodiments and of being practiced or being carried out in various ways.

It has been surprisingly discovered that sulfated poloxamers are able mitigate the negative effect of SLS on proteins, while maintaining or even exceeding the foaming properties of SLS, either as binary blends, or as ternary blends with other surfactants. For binary blends, a combination of a hydrophobic sulfated poloxamer and SLS provided copious amounts of foaming that was maintained in hard water. For ternary blends, a combination of a hydrophilic sulfated poloxamer, SLS, and a $C_{8-14}$ alkyl polyglucoside provided copious amounts of foaming that was maintained in hard water. Thus, the sulfated poloxamers may be used as partial replacements of SLS in personal care applications. They may be particularly useful in oral care applications, as they reduce irritation by SLS but maintain the foaming of SLS, and also do not have a negative taste to the user, unlike other surfactants used in the past.

Poloxamers are nonionic triblock copolymers composed of two hydrophilic poly(ethylene oxide) chains off of a hydrophobic poly(propylene oxide) chain. Poloxamers are available under the trade name Pluronic® from BASF.

Accordingly, one aspect of the invention relates to a personal care composition comprising a first surfactant comprising sodium lauryl sulfate and a second surfactant having a structure represented by Formula (I):

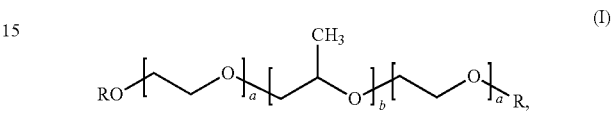

(I)

wherein each a has a value of about 1 to about 110, b has a value of about 16 to about 70, and at least one R group is $SO_3$, and the other R group is $SO_3$ or hydrogen. That is, Formula (I) represents a sulfated poloxamer.

The sulfated poloxamers according to one or more embodiments of the invention can be produced by sulfating poloxamers with chlorosulfonic acid. In one or more embodiments, poloxamers may also be sulfated using sulfur trioxide ($SO_3$), sulfamic acid, oleum or sulfuric acid. While not wishing to be bound to any particular theory, it is thought that sulfation can occur at either of the two —OH terminal groups of the poloxamer polymer. In one or more embodiments, sulfation occurs at only one of the —OH groups (i.e., monosulfated). Alternatively, in one or more embodiments, sulfation occurs at both ends (i.e., disulfated). Thus, in one embodiment, only one of the R groups in Formula (I) above is —$SO_3$, and the other is hydrogen. In an alternative embodiment, both R groups are —$SO_3$. In one or more embodiments, not all of the poloxamer molecules undergo sulfation. Thus, in these embodiments, the personal care composition also comprises unsulfated poloxamer molecules. In one or more embodiments, the personal care composition will comprise mostly mono-sulfated poloxamers, with small amounts of un-sulfated and di-sulfated poloxamers.

The ratio of the first and second surfactant in the personal care composition can be varied. Accordingly, in one or more embodiments of the personal care composition, SLS and the sulfated poloxamer of Formula (I) are present in a ratio of about 1:2 to about 4:1, about 1:1 to about 3:1, or about 1:1 to about 2:1. In a specific embodiment, the ratio of SLS and sulfated poloxamer is 2:1.

The ratio of the "a" and "b" groups in Formula (I), corresponding to etheylene oxide and propylene oxide blocks respectively, can be varied. In one or more embodiments, the sulfated poloxamer has a high percentage of ethylene oxide blocks, which renders the poloxamer hydrophilic. Thus, in one or more embodiments the second surfactant of Formula (I) has a ratio of a to b of about 10:90 to about 30:70. In further embodiments, the ratio of a to b is about 10:90, 20:80, or 30:70. In one or more embodiments, the only surfactants that personal care compositions contain are sulfated poloxamers with a high percentage of ethylene oxide blocks and SLS. Alternatively, in one or more embodiments, the personal care composition contains three surfactants, known as a ternary blend. In a further embodiment, the three surfactants comprise: SLS, a sulfated poloxamers with a high percentage of ethylene oxide blocks, and an alkyl polyglucoside.

In one or more other embodiments, the sulfated poloxamer has a low percentage of ethylene oxide blocks, which renders the poloxamer hydrophobic. Accordingly, in one or more embodiments, the second surfactant of Formula (I) has a ratio of a to b of about 60:40 to about 80:20. In further embodiments, the ratio of a to be is about 60:40, 70:30 or 80:20. In one or more embodiments, the only surfactants that personal care compositions contain are sulfated poloxamers with a low percentage of ethylene oxide blocks and SLS. Alternatively, in one or more embodiments, the personal care composition contains three surfactants. In a further embodiment, the three surfactants comprise: SLS, a sulfated poloxamers with a low percentage of ethylene oxide blocks, and an alkyl polyglucoside.

Embodiments with ratios of a to b that fall between the high and low range of ethylene oxide are considered to be mid range. Embodiments with a mid range of ethylene oxide will typically have a ratio of a to be of about 40:60 or 50:50. In one or more embodiments, the only surfactants that personal care compositions contain are sulfated poloxamers with a mid range percentage of ethylene oxide blocks and SLS. Alternatively, in one or more embodiments, the personal care composition contains three surfactants. In a further embodiment, the three surfactants comprise: SLS, a sulfated poloxamers with a mid range percentage of ethylene oxide blocks, and an alkyl polyglucoside.

Generally, it has been discovered that sulfated poloxamers with lower percentages of ethylene oxide blocks can generate more foam than their non-sulfated counterparts, are able to maintain foam generated by SLS, either alone or with alkyl polyglucosides, all while mitigating the protein denaturing effects of SLS. Sulfated poloxamers with higher percentages of ethylene oxide blocks generally will maintain SLS foaming characteristic in ternary blends with other surfactants, for example an APG. Although not wishing to be bound to any particular theory, it is possible that because poloxamers with a higher percentage of ethylene oxide units will have greater water solubility, which may impact its ability to be surface active. Mid range sulfated poloxamers will exhibit behavior between the high and low.

Unlike other surfactants that have been used in the past, sulfated poloxamers do not have a negative taste. This makes their use in oral care compositions particularly suitable. Thus, in one or more embodiments, the personal care composition further comprises typical oral care additives, for example abrasives and/or fluoride. Although some embodiments described herein relate to ternary blends with alkyl polyglucosides, the amount of alkyl polyglucoside needed can be reduced such that the ternary blends do not themselves have a commercially and/or unacceptably negative or bitter taste. Accordingly, in one or more embodiments, the ratio of SLS to sulfated poloxamer to alkyl glucoside ranges from about 1:1:1 to 2:1:1 to 3:1:1.

In one or more embodiments, the personal care compositions described above may be for any commercially suitable care item that normally utilizes SLS. In one embodiment, the personal care composition is for oral care.

Another aspect of the invention relates to methods of producing the personal care compositions described herein. The method comprises adding to a pharmaceutically or cosmetically acceptable base, a first surfactant comprising sodium lauryl sulfate and a second sulfated poloxamer surfactant of formula (I) as described above. Any of the above variants in the sulfated poloxamer can be used. Thus, for example in one or more embodiments, both R groups are $SO_3$. In one or more embodiments, the first and second surfactants are present in a ratio of about 1:2 to about 4:1.

There are additional optional processes that may be included in this aspect. For example, in one or more embodiments, the method further comprises adding an alkyl polyglucoside to the base. In one or more embodiments, the method further comprises adding a biomolecule to the base.

In embodiments where the personal care composition is an oral care composition, the method may further comprise adding components useful for that application. For example, fluoride and/or abrasives may be added.

Sulfated poloxamers exhibit anti-irritancy properties and are able to mitigate protein denaturing by SLS. This is particularly surprising because sulfates and are known in the art to be very irritating. In contrast, sulfated poloxamers are able to actually lower the irritancy of other compounds.

Zein numbers provide a way of measuring the irritancy of a given compound. Zein numbers are measured by titrating solutions of a compound (1% in water) with solid Zein protein until saturated. The amount of Zein protein that is added is measured gravimetrically. Solubilization of higher amounts of Zein protein results in a higher Zein number, which is associated with greater amounts of irritation. Thus, the Zein values for the SLS/Pluronic® blend being significantly lower than the Zein value for SLS alone demonstrate a great reduction in irritancy.

Higher zein numbers are generally associated with greater irritation of skin and mucous membranes. Thus, a reduction in a Zein number indicates that irritation has been reduced. For example, the Zein numbers of a 1:1 SLS:sulfated Pluronic® L121 blend are generally about 75 to about 90 versus greater than 500 for neat SLS. This demonstrates a significant reduction in irritation caused by SLS by adding sulfated poloxamer. Furthermore, the Zein value of the SLS/sulfated poloxamer blend is less than that of other SLS/surfactant mixtures. For example, a SLS:Glucopon® 420UP (an APG) mixture has a Zein value ranging from about 268 to about 288, which is also much greater than the SLS/Sulfated Pluronic® blend. This shows that the SLS/sulfated poloxamer blends will exhibit less irritancy than SLS/APG blends. Irritancy reduction is also observed when sulfated poloxamers are used in ternary systems with APGs. For example, the Zein numbers of 2:1:1 blend of SLS:Pluronic® F127S:Gluocpon® 420UP (an APG) are about 215-235, significantly less than either the SLS or APG alone.

Because of the anti-irritancy effects sulfated poloxamers have on SLS, it is possible to incorporate proteins into one or more of the compositions described herein. Thus, for example, in one or more embodiments, the personal care composition further comprises a protein, and in further embodiments, a biomolecule.

A third aspect of the invention thus relates to a method of ameliorating skin or mucosal membrane irritation due to sodium lauryl sulfate. The method comprises providing a composition that contacts skin or mucosal membrane upon use, the composition comprising a first surfactant comprising sodium lauryl sulfate and a second surfactant having a structure represented by formula (I):

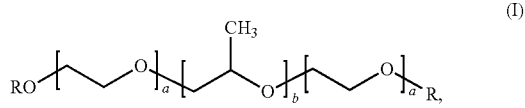

wherein each a has a value of about 1 to about 110, b has a value of about 16 to about 70, and at least one R group is $SO_3$, and the other R group is $SO_3$ or hydrogen; and wherein the second surfactant is present in an amount that is effective to ameliorate irritation of the skin or mucosal membrane. Any of the variants of formula (I) may be utilized in this method. For example, in one or more embodiments, both R groups are $SO_3$. In one or more embodiments, the first and second surfactants are present in a ratio of about 1:2 to about 4:1, about 1:1 to about 3:1, or about 1:1 to about 2:1.

In one or more embodiments of the invention, upon contact with the skin or mucosal membrane, the composition results in less skin or mucosal membrane irritation as compared to contact by the skin or mucosal membrane with a comparable composition comprising sodium lauryl sulfate without the second surfactant.

EXAMPLES

Samples of sulfated Pluronic® F127 and L121 were sulfated using chlorosulfonic acid. Pluronic® F127 contains a ratio of ethylene oxide to propylene oxide blocks of 70:30 and has an average molecular weight of about 12,000 Daltons. Unsulfated Pluronic® F127 will be referred to as "F127," and sulfated Pluronic® F127 as "F127S." Pluronic® L121 contains a ratio of ethylene oxide to propylene oxide blocks of about 10:90, and has an average molecular weight of about 4,400 Daltons. Unsulfated Pluronic® L121 will be referred to as "L121," and sulfated Pluronic® L121 as "L121S."

Foam properties were evaluated using a Sita Foam Tester R-2000 (SITA Messtechnik GmbH, Dresden, Germany) at 24° C. Test solutions were prepared by transferring 1.00 grams of active surfactant into a 1500 ml beaker and diluting to 1000 grams with either de-ionized water or a 150 ppm hard water solution (3:2 Ca—Mg). The SITA foam program is set as follows in Table 1:

TABLE 1

| SITA Foam Program Parameters | |
|---|---|
| Sample size | 250 mls |
| Mixing rotor speed | 1300 rpm |
| Number of cycles | 10 |
| Stir time | 10 seconds |
| Number of samples | 3 |

Example 1

Neat Surfactants in Soft Water

As a baseline, several neat surfactants were evaluated for their foam properties according to the above testing parameters in deionized water (i.e., containing no $CaCO_3$), thus simulating soft water. The tested surfactants included SLS, L121, L121S, F127, F127S and Glucopon® 420 UP. Glucopon® 420 UP is a C8-14 alkyl polyglucoside (un-preserved, 50% aq.), and is referred to as "G420UP."

The results are shown in FIG. 1, which exhibits foam volume as a function of the number of cycles. As seen in FIG. 1, L121S significantly outperformed its non-sulfated counterpart by generating much higher foam volume. F127S did not generate as much foam as its non-sulfated counterpart after the third cycle. All of the neat poloxamers generated less foam than either neat SLS or G420UP.

Example 2

Neat Surfactants in Hard Water

As another baseline, several neat surfactants were evaluated for their foam properties according to the above testing parameters in a solution containing 150 ppm $CaCO_3$, thus simulating hard water. The tested surfactants included SLS, L121, L121S, F127, F127S and G420UP.

Figure 2:
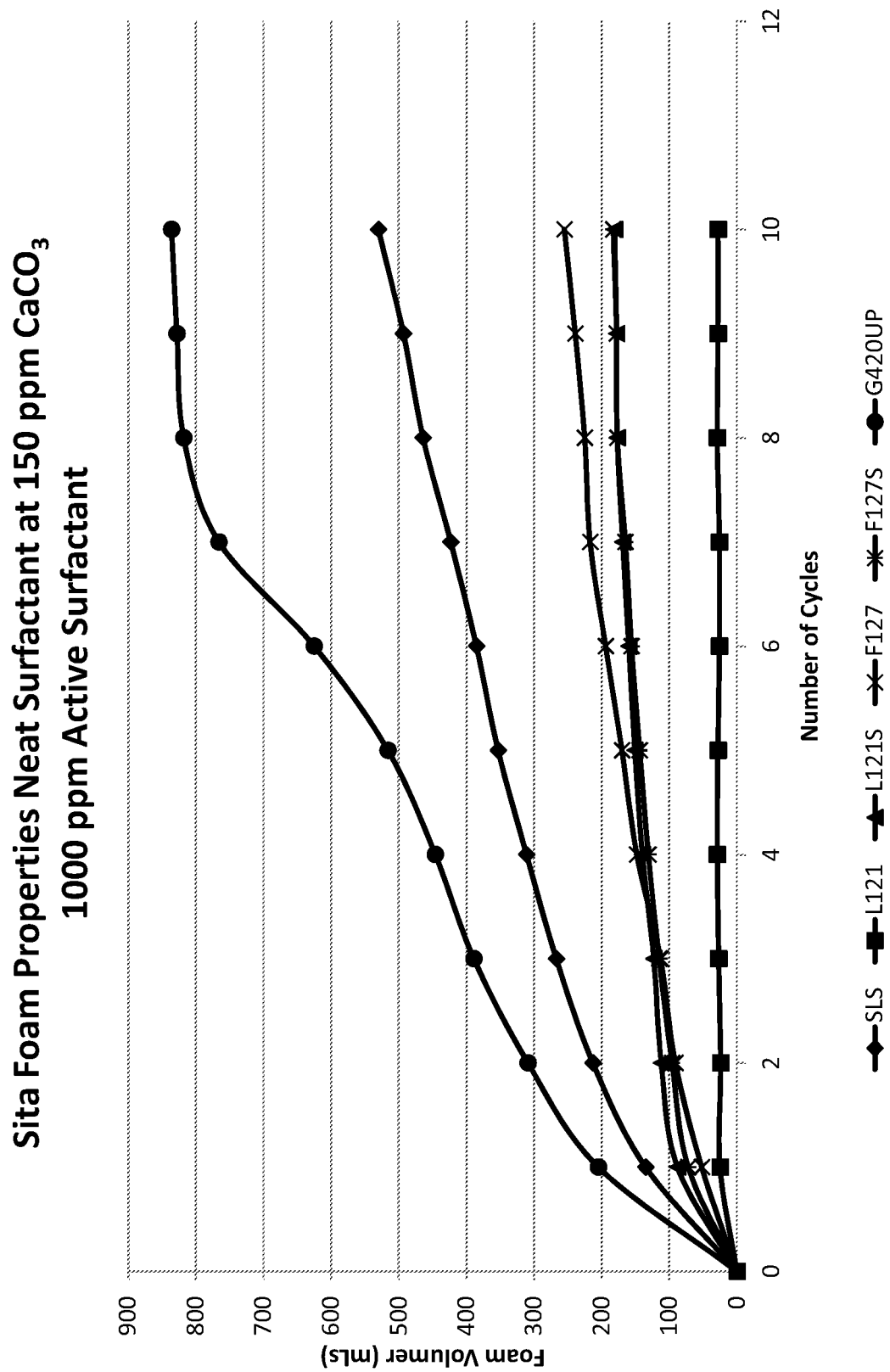
FIG. 2 shows the foam values in hard water of sodium lauryl sulfate, an AGP, several unsulfated poloxamers and sulfated poloxamers according to one or more embodiments of the invention.

The results are shown in FIG. 2, which exhibits foam volume as a function of the number of cycles. As seen in FIG. 2, L121S again significantly outperformed its non-sulfated counterpart. F127S generated slightly less foam as its non-sulfated counterpart after the third cycle. All of the neat poloxamers generated less foam than either neat SLS or G420UP.

Example 3

SLS Blends with Sulfated Pluronic® L121

SLS and several blends of SLS with L121S (at 1:1, 2:1 and 3:1 ratios) were evaluated for their foam properties according to the above testing parameters in a solution containing 150 ppm $CaCO_3$, thus simulating hard water.

Figure 3:
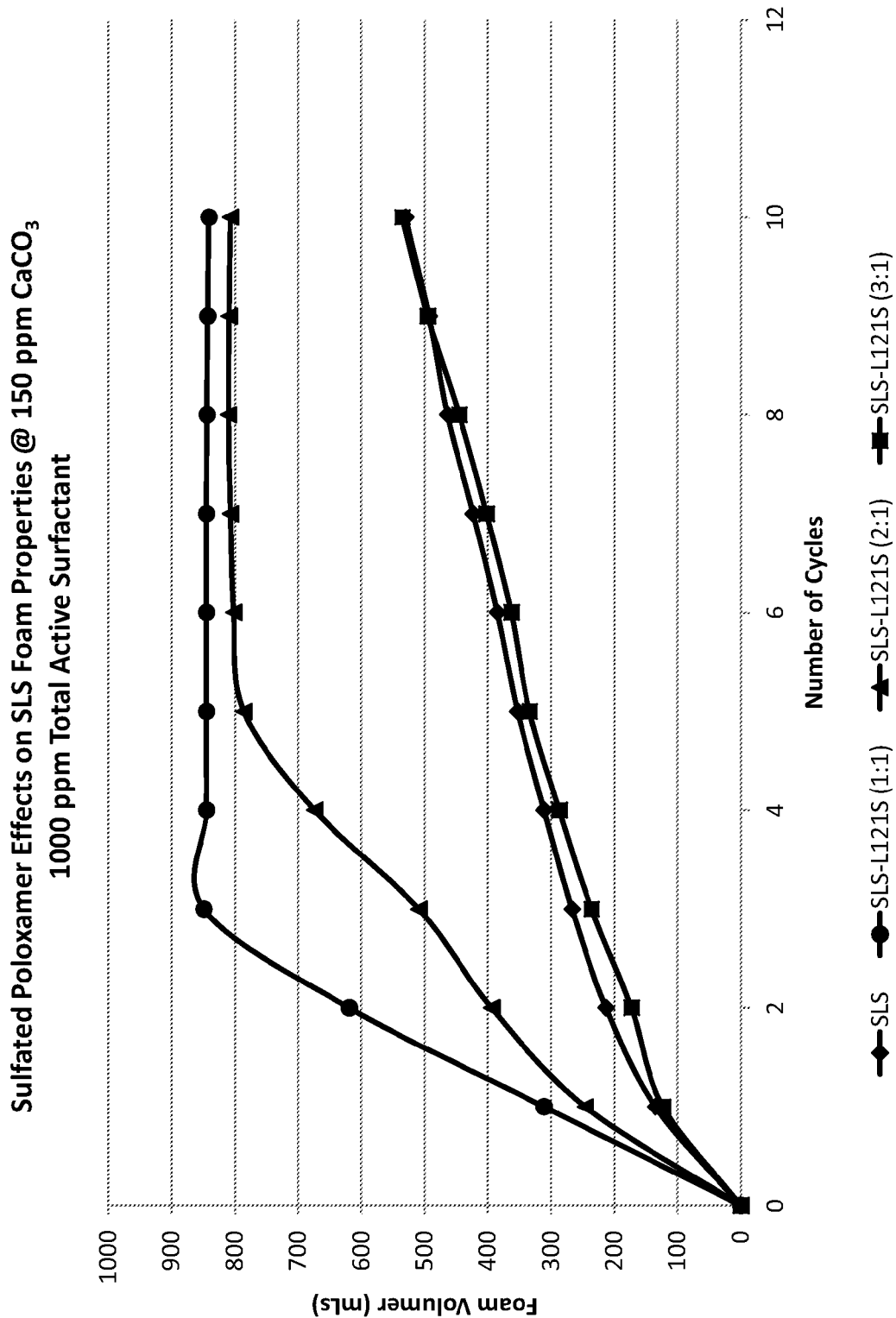
FIG. 3 shows the foam values of neat sodium lauryl sulfate and various blends of sodium lauryl sulfate with sulfated poloxamers according to one or more embodiments of the invention.

The results are shown in FIG. 3, which exhibits foam volume as a function of the number of cycles. As seen in FIG. 3, the 1:1 SLS-L121S and 2:1 SLS-L121S blends generated more foam than neat SLS or as compared to the addition of foam generated by neat SLS plus that generated by neat L121S, and generated foam much more quickly than SLS. The 3:1 SLS-L121S blend was able to generate foam similarly to SLS.

Example 4

SLS Blends with Sulfated Pluronic® F127

SLS and several blends of SLS with F127S (at 1:1, 2:1 and 3:1 ratios) were evaluated for their foam properties according to the above testing parameters in a solution containing 150 ppm $CaCO_3$, thus simulating hard water.

Figure 4:
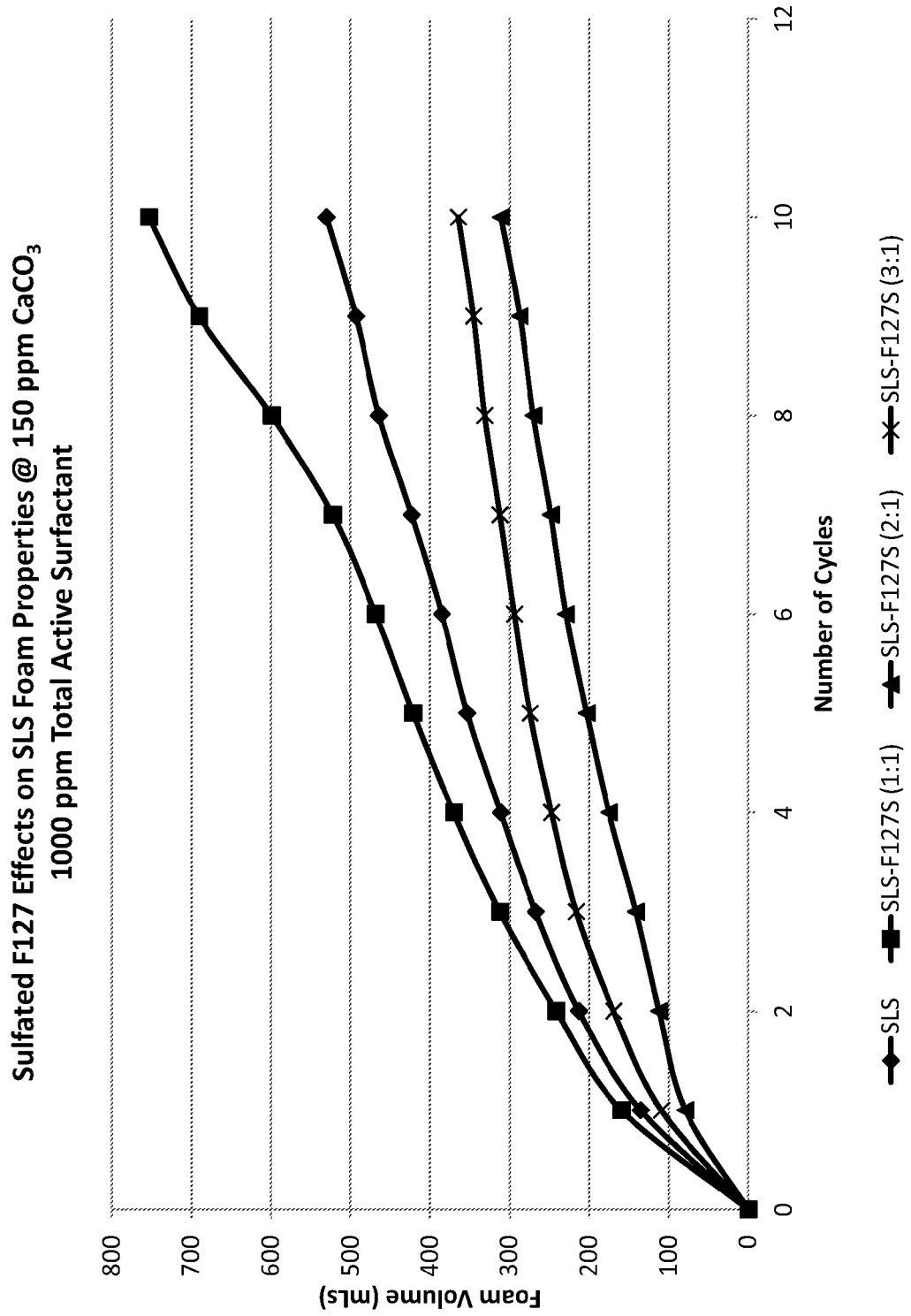
FIG. 4 shows the foam values of neat sodium lauryl sulfate and various blends of sodium lauryl sulfate with sulfated poloxamers according to one or more embodiments of the invention.

The results are shown in FIG. 4, which exhibits foam volume as a function of the number of cycles. As seen in FIG. 4, the 1:1 SLS-F127S generated more foam than neat SLS, and generated foam more quickly. The 2:1 and 3:1 SLS-F127S blends generated less foam volume as SLS.

Example 5

SLS Blends with Alkyl Polyglucoside (Comparative)

SLS and several blends of SLS with G420UP (at 1:1, 2:1 and 3:1 ratios) were evaluated for their foam properties according to the above testing parameters in a solution containing 150 ppm $CaCO_3$, thus simulating hard water. This example is considered to be comparative, because it does not contain a sulfated poloxamer according to one or more embodiments of the invention.

Figure 5:
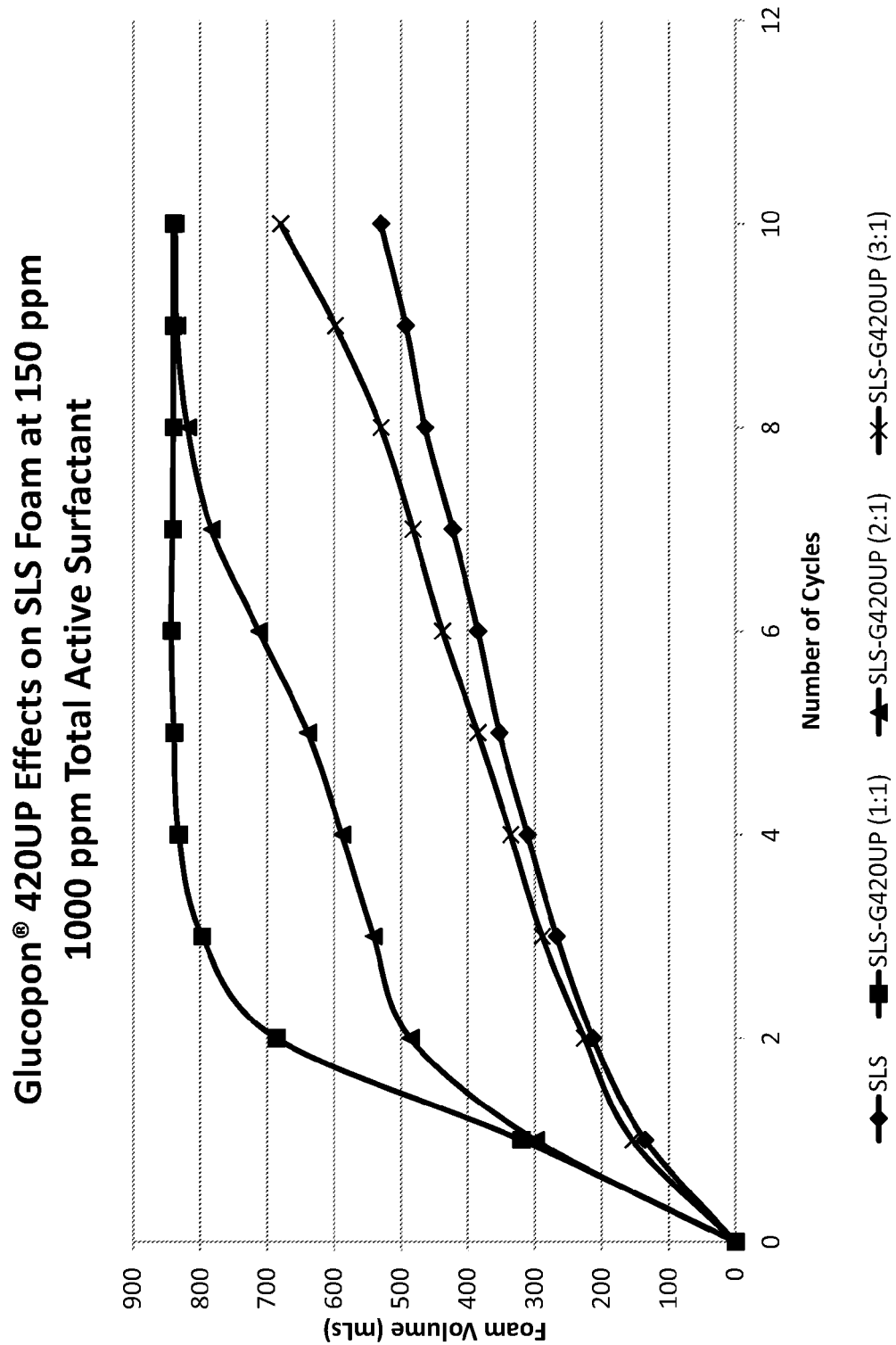
FIG. 5 shows the foam values of neat sodium lauryl sulfate and various blends of sodium lauryl sulfate and an alkyl polyglucoside.

The results are shown in FIG. 5, which exhibits foam volume as a function of the number of cycles. As seen in FIG. 5, all of the SLS-G420UP blends generated more foam volume than SLS.

Example 6

Ternary Blends with SLS, Sulfated Pluronic® L121 and Alkyl Polyglucoside

SLS and several ternary blends of SLS with L121S and G420UP (at 1:1:1, 2:1:1 and 3:1:1 ratios) were evaluated for their foam properties according to the above testing parameters in a solution containing 150 ppm $CaCO_3$, thus simulating hard water.

Figure 6:
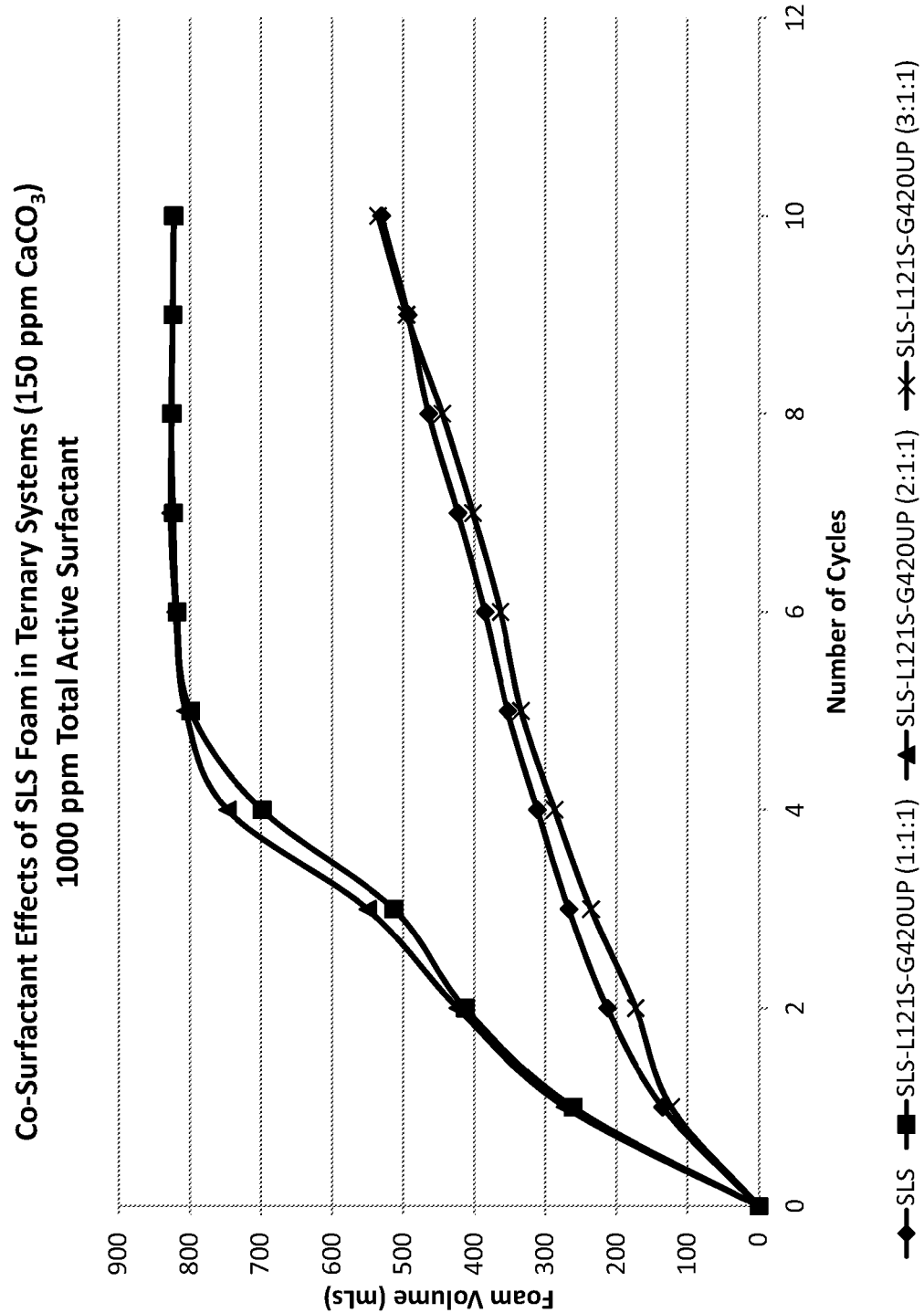
FIG. 6 shows the foam values of neat sodium lauryl sulfate and various ternary blends of sodium lauryl sulfate, an alkyl polyglucoside and a sulfate poloxamer according to one or more embodiments of the invention.

The results are shown in FIG. 6, which exhibits foam volume as a function of the number of cycles. As seen in FIG. 6, the 1:1:1 and 2:1:1 blends generated more foam than neat SLS, and generated foam much more quickly than neat SLS. Additionally, the 3:1:1 blend generated foam similarly to neat SLS.

Example 7

Ternary Blends with SLS, Sulfated Pluronic® F127 and Alkyl Polyglucoside

SLS and several ternary blends of SLS with F127S and G420UP (at 1:1:1, 2:1:1 and 3:1:1 ratios) were evaluated for their foam properties according to the above testing parameters in a solution containing 150 ppm $CaCO_3$, thus simulating hard water.

Figure 7:
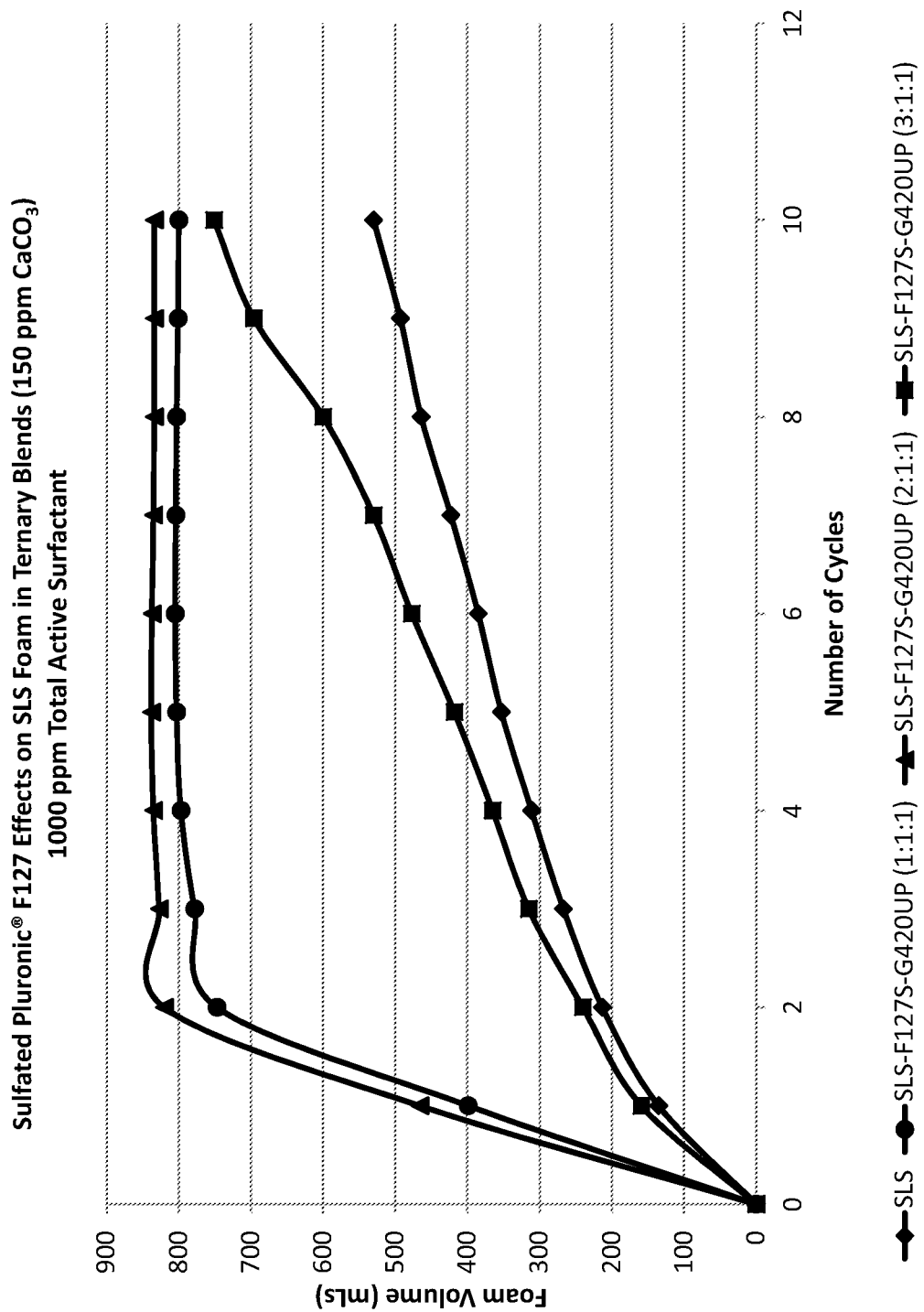
FIG. 7 shows the foam values of neat sodium lauryl sulfate and various ternary blends of sodium lauryl sulfate, an alkyl polyglucoside and a sulfate poloxamer according to one or more embodiments of the invention.

The results are shown in FIG. 7, which exhibits foam volume as a function of the number of cycles. As seen in FIG. 7, all of the blends generated more foam than neat SLS. Additionally, the 1:1:1 and 2:1:1 blends generated foam much more quickly than SLS.

Example 8

Ternary Blends with SLS, Alkyl Polyglucoside and Sulfated and Unsulfated Pluronic® F127

Two ternary blends were evaluated for their foam properties according to the above testing parameters in a solution containing 150 ppm $CaCO_3$, thus simulating hard water. The first blend had 1:1:1 SLS-F127-APG, and the second blend 1:1:1 SLS-F127S-APG.

Figure 8:
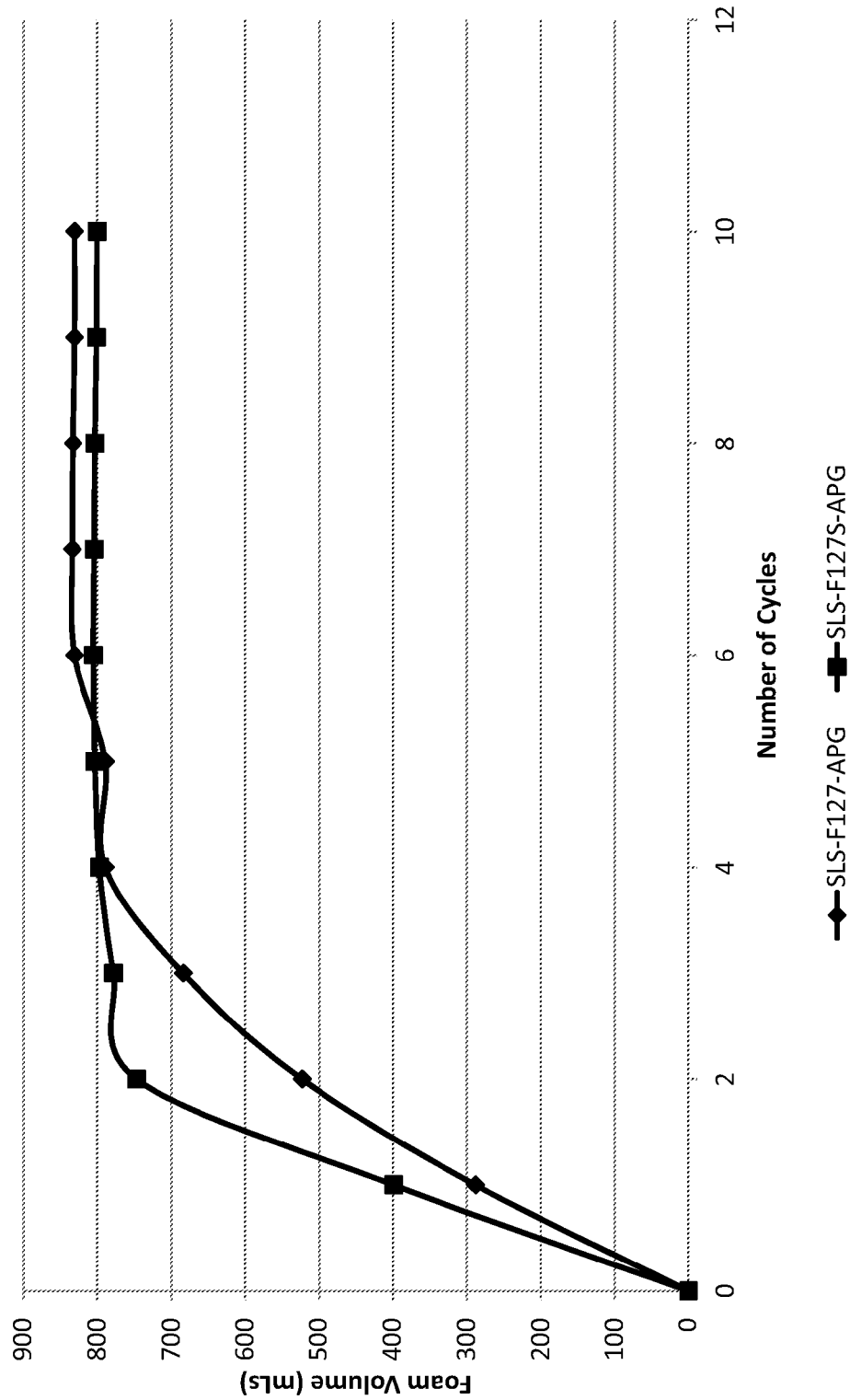
FIG. 8 shows the foam values of ternary blends of sodium lauryl sulfate, an alkyl polyglucoside, and sulfated and unsulfated poloxamers.

The results are shown in FIG. 8, which exhibits foam volume as a function of the number of cycles. As seen in FIG. 8, the blend with sulfated F127 generated more foam much more quickly than unsulfated F127.

As can be seen from the examples above, both sulfate derivatives maintained SLS foam in hard water when used ternary systems with $C_{8-14}$ alkyl polyglucoside. Sulfated Pluronic® L121 was generated higher foam volume at a lower number of cycles than its unsulfated counterpart, and was also capable of maintaining SLS foam in a binary system.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. An oral care composition comprising:
a first surfactant comprising sodium lauryl sulfate;
a second surfactant having a structure represented by

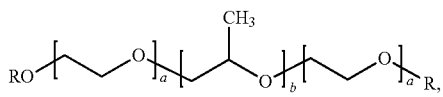

wherein each a has a value of about 1 to about 110, b has a value of about 16 to about 70, and at least one R group is $SO_3$, and the other R group is $SO_3$ or hydrogen.

2. The care composition of claim 1, wherein both R groups are $SO_3$.

3. The care composition of claim 1, wherein the second surfactant has a ratio of a to b of about 10:90 to about 30:70.

4. The care composition of claim 1, wherein the second surfactant has a ratio of a to b of about 60:40 to about 80:20.

5. The care composition of claim 1, further comprising alkyl polyglucoside.

6. The care composition of claim 5, wherein the first surfactant, second surfactant and alkyl polyglucoside are present in a ratio of about 1:1:1 to about 3:1:1.

7. The care composition of claim 1, further comprising a biomolecule.

8. The care composition of claim 1, wherein the first and second surfactants are present in a ratio of about 1:2 to about 4:1.

9. The care composition of claim 8, wherein the first and second surfactants are present in a ratio of about 1:1 to about 3:1.

10. The care composition of claim 1, further comprising an abrasive and/or fluoride.

11. A method of ameliorating skin or mucosal membrane irritation in an oral care composition due to sodium lauryl sulfate, the method comprising:
providing an oral care composition that contacts skin or mucosal membrane upon use, the composition comprising a first surfactant comprising sodium lauryl sulfate and a second surfactant having a structure represented by

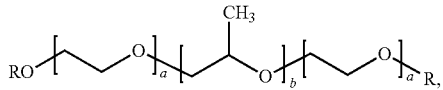

wherein each a has a value of about 1 to about 110, b has a value of about 16 to about 70, and at least one R group is $SO_3$, and the other R group is $SO_3$ or hydrogen; and
wherein the second surfactant is present in an amount that is effective to ameliorate irritation of the skin or mucosal membrane.

12. The method of claim 11, wherein both R groups are $SO_3$.

13. The method of claim 11, wherein the first and second surfactants are present in a ratio of about 1:2 to about 4:1.

14. The method of claim 11, wherein upon contact with the skin or mucosal membrane, the composition results in less skin or mucosal membrane irritation as compared to contact by the skin or mucosal membrane with a comparable composition comprising sodium lauryl sulfate without the second surfactant.

15. A method of making an oral care composition of claim 1, the method comprising adding to a pharmaceutically or cosmetically acceptable base, a first surfactant comprising sodium lauryl sulfate and a second surfactant having a structure represented by

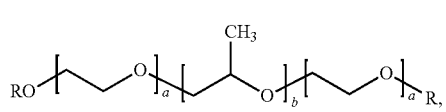

wherein each a has a value of about 1 to about 110, b has a value of about 16 to about 70, and at least one R group is $SO_3$, and the other R group is $SO_3$ or hydrogen.

16. The method of claim 15, further comprising adding alkyl polyglucoside to the base.

17. The method of claim 15, further comprising adding a biomolecule to the base.

18. The method of claim 15, wherein the first and second surfactants are present in a ratio of about 1:2 to about 4:1.

* * * * *